United States Patent [19]

Winston

[11] Patent Number: 5,424,270
[45] Date of Patent: Jun. 13, 1995

[54] BICARBONATE FUNGICIDE COMPOSITIONS CONTAINING SPREADER-STICKER INGREDIENTS

[75] Inventor: Anthony E. Winston, East Brunswick, N.J.

[73] Assignee: Church & Dwight Co., Inc., Princeton, N.J.

[21] Appl. No.: 86,884

[22] Filed: Jul. 7, 1993

Related U.S. Application Data

[62] Division of Ser. No. 984,532, Dec. 2, 1992, abandoned.

[51] Int. Cl.⁶ .................... A01N 37/02; A01N 37/06; A01N 59/00; C05G 3/02
[52] U.S. Cl. .................................. 504/101; 424/715; 424/716; 424/717; 71/DIG. 1; 514/557; 514/558; 514/560; 514/772; 514/772.1; 514/772.3; 514/772.6; 514/773; 514/775; 514/777; 514/778; 514/779; 514/780; 514/781; 514/782; 514/784
[58] Field of Search ............... 424/601, 703, 705, 715, 424/716, 717; 514/558, 560, 557, 772.1, 772.3, 772.6, 772, 773, 775, 777–782, 784; 504/101; 71/DIG. 1

[56] References Cited

U.S. PATENT DOCUMENTS

| | | | |
|---|---|---|---|
| 1,560,558 | 11/1925 | Fulton et al. | 424/715 |
| 3,635,690 | 1/1972 | Griffith | 71/1 |
| 4,318,729 | 3/1982 | Coury | 71/29 |
| 4,599,233 | 7/1986 | Misato et al. | 424/717 |
| 4,692,466 | 9/1987 | Yoshimoto et al. | 514/604 |
| 5,030,658 | 7/1991 | Salloum et al. | 514/560 |
| 5,093,124 | 3/1992 | Kulenkampff | 424/406 |
| 5,174,804 | 12/1992 | Rehberg et al. | 504/101 |

FOREIGN PATENT DOCUMENTS 53-96319 8/1978 Japan.
60-153785 8/1985 Japan.

OTHER PUBLICATIONS

Farm Chemicals Handbook '87, published by Meister Publishing Co., Ohio, 1987, pp. B10, B14, B19, B20, B34, B54, B68, B69, and C238–239.

*Primary Examiner*—Allen J. Robinson
*Assistant Examiner*—John D. Pak
*Attorney, Agent, or Firm*—Charles B. Barris

[57] ABSTRACT

The present invention provides a method for controlling fungal disease in plants with a fungicidal fertilizer composition which contains ingredients which are biocompatible for purposes of agricultural applications, and which are harmless to animals and humans. Illustrative of an invention composition is an aqueous solution which has a content of two alkali metal bicarbonate salts, an alkali metal fatty acid salt, and a water-soluble thickener such as xanthan gum. The combination of fatty acid salt and thickener functions as an effective spreader-sticker medium.

5 Claims, No Drawings

BICARBONATE FUNGICIDE COMPOSITIONS CONTAINING SPREADER-STICKER INGREDIENTS

This application is a division of application Ser. No. 07/984,532, filed Dec. 2, 1992, now abandoned.

BACKGROUND OF THE INVENTION

The control of phytopathogenic fungi is of great economic importance since fungal growth on plants or on parts of plants inhibits production of foliage, fruit or seed, and the overall quality of a cultivated crop.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain an inorganic bicarbonate or carbonate compound. It is known that bicarbonate and carbonate compounds exhibit fungicidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillum italicum* and *Penicillum digitalum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

Japanese patent 53090319 describes the application of potassium bicarbonate as an active biocide for the control of fungal diseases common to tomato and cucumber plants.

Japanese patent 53118523 describes the combination of sodium bicarbonate and lecithin as an active agent for the control of agricultural and fruit storage fungus diseases.

Japanese patent 56043207 describes a biocidal composition containing sodium bicarbonate and a polyglycerol fatty acid ester. The biocide controls *Penicillum digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

German patent DE 2927994 describes a fungicide which consists of sodium bicarbonate incorporated into a food-compatible surfactant such as saccharose laurate.

Japanese patent 57062208 describes horticultural fungicides in which the addition of sodium bicarbonate to polyoxin or thiophanatemethyl increases the fungicidal activity of the organic biocide against botrytis cinerea on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wilt, rice sheath blight, rice blast and citrus canker.

There remains a continuing need for the development of new and more effective fungicides which possess preventive, curative and systemic activity for the protection of cultivated plants, with a minimum of phytotoxic side effects.

Accordingly, it is an object of this invention to provide a dry blend biocide composition which contains a bicarbonate ingredient exhibiting fungicidal properties.

It is another object of this invention to provide a fungicide composition which is an aqueous formulation of ingredients which include a bicarbonate salt, and a combination of a fatty acid salt and pseudoplastic thickener which functions as a spreader-sticker medium when the aqueous medium is applied to plant foliage.

Other objects and advantages of the present invention shall become apparent from the accompanying description and examples.

DESCRIPTION OF THE INVENTION

One or more objects of the present invention are accomplished by the provision of an aqueous fungicidal formulation having a content comprising (1) an ingredient selected from alkali metal and ammonium bicarbonates; (2) an ingredient selected from alkali metal and ammonium salts of $C_8$–$C_{22}$ fatty acids; and (3) a water-soluble pseudoplastic thickener ingredient.

An invention aqueous fungicidal formulation can contain about 0.1–25 weight percent of bicarbonate ingredient, about 0.05–50 weight percent of $C_8$–$C_{22}$ fatty acid salt ingredient, and about 0.01–5 weight percent of thickener ingredient, based on the formulation weight.

In another embodiment this invention provides a concentrated aqueous fungicidal formulation having a content comprising (1) about 2–25 weight percent of an ingredient selected from alkali metal and ammonium bicarbonates; (2) about 0.2–50 weight percent of an ingredient selected from alkali metal and ammonium salts of $C_8$–$C_{22}$ fatty acids; and (3) about 0.04–5 weight percent of a water-soluble pseudoplastic thickener ingredient; based on the formulation weight.

An invention concentrated aqueous fungicidal formulation is in a convenient and economical form for storage and transportation. A concentrated formulation is adapted for dilution with water up to one hundred fold and more for agricultural and horticultural applications such as spraying plant foliage.

In another embodiment this invention provides a dilute aqueous fungicidal formulation for direct usage in agricultural applications, which has a content comprising (1) about 0.2–1 weight percent of an ingredient selected from alkali metal and ammonium bicarbonates; (2) about 0.05–2 weight percent of an ingredient selected from alkali metal and ammonium salts of $C_8$–$C_{22}$ fatty acids; and (3) about 0.01–0.5 weight percent of a water-soluble pseudoplastic thickener ingredient; based on the formulation weight.

An invention dilute aqueous fungicidal solution is in a ready-to-use form which can be applied directly to the foliage of plants, bushes and trees, such as by electrodynamic spraying techniques.

In another embodiment this invention provides a fungicide composition which is a dry blend formulation comprising (1) an ingredient selected from alkali metal and ammonium bicarbonates; (2) an ingredient selected from alkali metal and ammonium salts of $C_8$–$C_{22}$ fatty acids; and (3) a water-soluble pseudoplastic thickener ingredient.

An invention dry blend fungicide composition can contain about 20–85 weight percent of bicarbonate ingredient, about 16–75 weight percent of $C_8$–$C_{22}$ fatty acid salt ingredient, and about 0.5–20 weight percent of thickener ingredient, based on the composition weight.

A dry blend fungicide composition can be diluted with water to form aqueous fungicidal solutions with controlled rheological properties. An aqueous fungicidal solution typically contains less than about 5 weight percent of active ingredients, based on the solution weight. For most applications the content of bicarbonate ingredient is maintained at a concentration below about one weight percent, as a means of minimizing phytotoxic effects on treated plants which are sensitive to alkaline pH conditions.

An invention dry blend fungicide composition also can be in the form of dusting powders, which optionally can include a solid diluent such as bentonite, calcium carbonate, magnesia, gypsum, kieselguhr, diatomaceous earth, and the like. Plant foliage can be treated with a dusting powder, and ambient weather cycles and atmospheric conditions provide sufficient moisture to convert the applied dusting powder to an adherent coating on the plant foliage. A dusting powder preferably has an average particle size diameter between about 1–100 microns, and has a content of submicron particles.

The inorganic salt ingredient of an invention fungicide composition is selected from compounds which include sodium bicarbonate, potassium bicarbonate, lithium bicarbonate and ammonium bicarbonate. In a further embodiment, the inorganic salt ingredient can include an additional compound selected from sodium carbonate, potassium carbonate, lithium carbonate and ammonium carbonate, in a quantity of about 1–30 weight percent based on the weight of bicarbonate ingredient.

Illustrative of inorganic salt ingredients in a formulation are sodium, potassium, lithium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt compound normally is determined by pH control considerations when aqueous formulations are prepared. The content of a carbonate salt compound can be varied to control the pH at a desired level in the range of 7.5–12. Aqueous fungicidal formulations of the present invention tend to have a higher fungicidal activity at higher pH values.

The $C_8$–$C_{22}$ fatty acid salt ingredient is selected from alkali metal and ammonium salts of natural straight chain and synthetic branched chain fatty acids, which have a saturated or unsaturated structure. The $C_8$–$C_{22}$ fatty acid salt ingredient can be incorporated in a quantity between about 10–75 weight percent, based on the weight of active ingredients.

Illustrative of natural fatty acids are caprilic acid, pelargonic acid, capric acid, lauric acid, myristic acid, palmitic acid, stearic acid, oleic acid, linoleic acid, arachidic acid, behenic acid, cetoleic acid, and the like.

The $C_8$–$C_{22}$ fatty acid salt ingredient can consist of two or more saturated or unsaturated carboxylic acids such as those derived from beef and mutton tallow, lard, cottonseed oil, palm oil, and the like.

Palm fatty acid distillate is a commercial product produced by distilling the fatty acids present in natural palm oil. A distillate product typically has the following weight percent content:

| Free fatty acids | 60–90 |
| --- | --- |
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram. The fatty acids in the free fatty acids and the triglycerides consist of the following weight percent:

| Palmitic acid | 38–50 |
| --- | --- |
| Oleic acid | 35–40 |
| Linoleic acid | 5–10 |
| Stearic acid | 3–6 |
| Lauric acid | 1–3 |

Beef tallow acids are available commercially as a byproduct obtained by alkaline extraction of waste beef fat and subsequent acidification, and normally contain the following weight percent of fatty constituents:

| Free fatty acids | 60–90 |
| --- | --- |
| Triglycerides | 10–40 |
| Water | <1 |
| Unsaponifiables | <3 |

The iodine value is less than 50 and the melting point is 40°–45° C. The content of peroxides is less than 10 milliequivalents of oxygen per kilogram. The fatty acids in the free fatty acids and in the triglycerides have the following weight percent content:

| Palmitic acid | 22–28 |
| --- | --- |
| Oleic acid | 38–44 |
| Linoleic acid | 3–6 |
| Stearic acid | 18–24 |

Because $C_8$–$C_{22}$ fatty acids and glycerides are susceptible to atmospheric oxidation, it is advantageous to incorporate an antioxidant, and/or a chelating agent to bind any ferric, copper, zinc or other metal capable of catalyzing atmospheric oxidation. Suitable quantities for inclusion in the fatty acid bulk are about 0.01–0.4% or higher of antioxidant as permitted by regulation, and/or about 0.05–0.3% of chelating agent, based on the weight of fatty acid. Optionally an antioxidant and/or chelating agent can be added to a dry blend or aqueous fungicide composition as additional ingredients during the formulation stage.

Illustrative of preferred additives are butylated hydroxytoluene, butylated hydroxyanisole and tertiarybutylhydroquinone antioxidant, and citric acid and ethylenediamine tetraacetate chelating agents. The chelating agent and antioxidant can be added per se, or in a solvent such as propylene glycol to facilitate incorporation into the fatty acid or formulated ingredients.

A $C_8$–$C_{22}$ fatty acid salt of an invention composition is prepared by reacting the free fatty acid component with an appropriate basic alkali metal or ammonium compound, such as a carbonate, bicarbonate or hydroxide derivative.

A $C_8$–$C_{22}$ fatty acid salt ingredient can be added to an invention composition as a previously prepared compound, or the salt can be formed in situ by the incorporation and blending of $C_8$–$C_{22}$ fatty acid and basic alkali metal or ammonium bicarbonate or carbonate ingredients. If a basic carbonate salt is employed for fatty acid salt formation, a reaction byproduct is an advantageous in situ generation of bicarbonate salt ingredient.

The thickener ingredient of an invention fungicide composition is selected from water-soluble organic polymers which exhibit pseudoplastic rheological properties in an aqueous medium.

The term "water-soluble" as employed herein refers to a thickener ingredient which has a solubility of at least about one gram per 100 grams of water at 25° C.

The term "pseudoplastic" as employed herein refers to the rheological behavior of an aqueous solution containing a dissolved thickener ingredient, in which the apparent viscosity of the aqueous solution decreases with increasing shear rate.

Illustrative of water-soluble polymers which exhibit pseudoplastic properties in an aqueous medium are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, methyl vinyl ether/maleic anhydride copolymer, styrene/maleic anhydride copolymer, ethylene/maleic anhydride copolymer, the corresponding alkali metal salts of the maleic anhydride copolymers, alkali metal salts of poly(meth)acrylate, and the like.

Many of the water-soluble polymers are large volume commercial products. Sodium carboxymethyl cellulose (CMC) is available in powder or granular form having a particle size of 50–200 microns. CMC is available in a degree of substitution (DS) range of 0.38–1.4.

A preferred fungicide composition of the present invention is one containing sodium or potassium bicarbonate, potassium oleate and xanthan gum ingredients.

The ingredients in an invention fungicide composition can be selected to include nitrogen, phosphorus and potassium elements in a ratio that qualifies the composition to function as a fertilizer in addition to its function as a fungicide, when applied to cultivated crops. When an aqueous solution containing fertilizer elements is sprayed on plant foliage, there is direct absorption of the fertilizer elements into the leaves.

In another embodiment this invention provides a fungicidal fertilizer composition which is a dry blend formulation comprising (1) about 20–85 weight percent of an ingredient selected from alkali metal and ammonium bicarbonates; (2) about 10–75 weight percent of an ingredient selected from alkali metal and ammonium salts of $C_8$–$C_{22}$ fatty acids; (3) about 0.5–20 weight percent of a water-soluble pseudoplastic thickener ingredient; and (4) about 20–85 weight percent of an ingredient selected from phosphorus-containing compounds based on the composition weight; wherein the composition ingredients have a formulated ratio of nitrogen, phosphorus and potassium elements. The formulated ratio depends on the intended application. A typical ratio is 10-15-10.

Besides nitrogen, phosphorus and potassium, an invention fungicidal fertilizer composition can contain trace elements, and other essential elements as exemplified by sulfur as contained in a compound such as sodium bisulfite or thiourea.

In a further embodiment this invention provides a fungicidal fertilizer composition which is an aqueous formulation having a content comprising (1) about 0.1–25 weight percent of an ingredient selected from alkali metal and ammonium bicarbonates; (2) about 0.05–50 weight percent of an ingredient selected from alkali metal and ammonium salts of $C_8$–$C_{22}$ fatty acids; (3) about 0.01–5 weight percent of a water-soluble pseudoplastic thickener ingredient; and (4) about 0.1–25 weight percent of an ingredient selected from phosphorus-containing compounds; based on the composition weight; wherein the composition ingredients have a formulated ratio of nitrogen, phosphorus and potassium elements as described above.

An invention fungicide composition can include one or more other biologically active ingredients, such as those which exhibit herbicidal, insecticidal or plant growth regulating activity.

A fungicide composition of the present invention has a novel combination of properties for the practice of pesticide control in agricultural and horticultural applications.

The bicarbonate ingredient exhibits fungicidal properties, and the efficacy of any additionally included organic pesticide ingredient usually is enhanced by the presence of the bicarbonate ingredient. A lesser quantity of optional pesticide ingredient can be employed to achieve a desired degree of pest control.

A present invention fungicide composition can be formulated to exhibit no phytotoxicity, or to minimize the toxic effects of salt stress on plants by the bicarbonate ingredient.

A present invention fungicide composition provides particular advantage for the control of infectious phytopathogenic fungi which thrive under acidic soil conditions.

All of the fungicide composition ingredients are biocompatible when the composition is applied in an agricultural environment. The bicarbonate, $C_8$–$C_{22}$ fatty acid salt and thickener ingredients are all harmless to animals and humans.

A significant feature of a present invention fungicide composition is the presence of $C_8$–$C_{22}$ fatty acid salt and thickener ingredients, which function as a spreader-sticker medium when the fungicide composition is applied to plant foliage as an aqueous solution. An applied aqueous solution forms an adherent coating of ingredients on plant foliage or fruit. The fatty acid salt ingredient aids in spreading and sticking the fungicide composition ingredients to the foliage or fruit to which it is applied. The pseudoplastic thickener ingredient increases the amount of aqueous fungicide composition which adheres to the plant surfaces because of its static high apparent viscosity. During a spraying procedure, the pseudoplastic thickener ingredient contributes a low mobile viscosity to the spray solution, which facilitates the spraying action. After spraying, the applied coating resists drifting under wind conditions, and exhibits humectant properties in addition to enhanced fungicidal activity.

Another important advantage of an invention fungicide composition derives from the water-solubility of the contained ingredients. A coating of an invention fungicide composition on plant foliage or fruit can be removed readily by water-washing. Conventional fungicide compositions which contain a petroleum-based spreader-sticker ingredient leave an oily residue on treated plant foliage or fruit which is difficult to remove.

The following examples are further illustrative of the present invention. The components and specific ingredients are presented as being typical, and various modifications can be derived in view of the foregoing disclosure within the scope of the invention.

EXAMPLE I

This Example illustrates the preparation of a fungicide powder concentrate in accordance with the present invention.

A blend of the following ingredients is prepared:

|  | Parts |
| --- | --- |
| sodium bicarbonate | 40 |
| potassium bicarbonate | 25 |
| sodium stearate | 25 |
| xanthan gum | 10 |

The formulated concentrated powder is diluted with water by the dispersion of 2 parts of the powder blend into 100 parts of water. The resulting solution is sprayed onto plant foliage where it forms an adherent coating on the foliage surfaces.

EXAMPLE II

This Example illustrates the preparation of fungicide composition tablets which rapidly disintegrate and disperse in water.

|  | Parts |
| --- | --- |
| sodium bicarbonate | 35 |
| palm fatty acid distillate sodium salt[(1)] | 10 |
| guar gum | 5 |
| citric acid | 10 |
| polyethylene glycol (M.W. 4000) | 10 |
| sodium lignosulfonate | 2 |

| Lauric acid | 2.3% |
| --- | --- |
| Palmitic acid | 49.9% |
| Stearic acid | 5.4% |
| Oleic acid | 35.0% |
| Linoleic acid | 7.4% |

The active ingredients are blended with the citric acid, polyethylene glycol and sodium lignosulfonate ingredients, and the blend is formed into tablets which disintegrate and disperse in water within about six minutes at 25° C. The aqueous medium forms an adherent coating of ingredients when sprayed on plant foliage.

EXAMPLE III

This Example illustrates the preparation of a fungicidal formulation in accordance with the present invention.

|  | Parts |
| --- | --- |
| potassium bicarbonate | 50 |
| potassium oleate | 15 |
| potassium stearate | 10 |
| potassium palmitate | 10 |
| sodium carboxymethyl-cellulose[(1)] | 15 |

|  | Parts |
| --- | --- |
| water | 50 |

[(1)]Aldrich Chemical Co., CMC of 3000–6000 centipoises, intrinsic viscosity of 2% aqueous solution at 25° C.

The solid ingredients are blended, and the blend is suspended in water to form an aqueous emulsion.

The emulsion formulation is diluted with water to 0.5% by weight of bicarbonate ingredient. The diluted formulation is tested as a fungicide medium against plant foliage infected with powdery mildew. The fungicidal medium is 100% effective in mildew eradication, and prevents re-infection.

EXAMPLE IV

This Example illustrates the preparation of a concentrated aqueous fungicidal formulation.

|  | Parts |
| --- | --- |
| potassium bicarbonate | 22.00 |
| potassium oleate | 17.00 |
| potassium octanoate | 3.00 |
| xanthan gum | 2.00 |
| butylated hydroxytoluene (BHT) | 0.02 |
| water | 57.98 |

Potassium octanoate is included in the formulation to serve as a hydrotrope to prevent precipitation of potassium oleate from solution. The potassium octanoate also enhances the spreading and sticking function of the potassium oleate.

The aqueous concentrate is prepared by dissolving 9.6 parts of potassium carbonate in the water, and then with stirring adding 2.4 parts of octanoic acid and 15 parts of oleic acid. The BHT and xanthan gum are added, followed by the addition of 15 parts of potassium bicarbonate.

The prepared concentrated aqueous formulation is diluted 1 part to 40 parts of water. The diluted formulation is effective for prevention of powdery mildew and other fungal diseases on roses, grapes and cucurbits.

Superior fungicidal results are obtained when the active ingredients are potassium or sodium bicarbonate, potassium oleate and xanthan gum.

EXAMPLE V

This Example illustrates the preparation of a partially diluted aqueous fungicidal formulation.

|  | Parts |
| --- | --- |
| potassium bicarbonate | 6.00 |
| potassium oleate | 5.00 |
| butylated hydroxytoluene (BHT) | 0.02 |
| potassium polyacrylate[(1)] | 2.00 |
| water | 86.98 |

[(1)]polyacrylic acid K salt; M.W. of 200,000.

The potassium polyacrylate is dissolved in the water. The potassium bicarbonate is added to the aqueous solution, followed by the addition of potassium oleate and BHT.

The aqueous solution is diluted with 9 parts of water per part of solution. The diluted solution is effective for controlling fungal diseases when sprayed on cultivated plants.

EXAMPLE VI

This Example illustrates the preparation of a dilute aqueous fungicidal formulation which is ready-to-use in agricultural applications.

| | Parts |
|---|---|
| sodium bicarbonate | 0.50 |
| potassium oleate | 0.50 |
| butylated hydroxytoluene (BHT) | 0.02 |
| sodium alginate | 0.40 |
| water | 98.50 |

The sodium alginate is dissolved in the water, followed by the successive addition of sodium bicarbonate, potassium oleate and BttT.

The dilute formulation is effective for control of powdery mildew and other fungal diseases when sprayed on plant foliage or fruit.

EXAMPLE VII

This Example illustrates the preparation of an aqueous fungicidal formulation which contains a mixture of bicarbonate compounds.

| | Parts |
|---|---|
| potassium bicarbonate | 6 |
| sodium bicarbonate | 6 |
| ammonium bicarbonate | 6 |
| ammonium palmitate | 12 |
| xanthan gum | 2 |
| water | 68 |

The ingredients are added to the water to form an aqueous formulation in the manner previously described.

The formulation is more effective than a comparative formulation containing a single bicarbonate compound, for controlling a broad range of foliar and soil-born resistant fungi.

EXAMPLE VIII

This Example illustrates the preparation of a fungicidal fertilizer composition for application to plant foliage and soil.

| | Parts |
|---|---|
| potassium bicarbonate | 10 |
| potassium oleate | 10 |
| potassium octanoate | 5 |
| carrageenan | 2 |
| urea | 5 |
| dipotassium orthophosphate | 2 |
| water | 66 |

The ingredients are dispersed in the water to form a concentrated solution. The solution is diluted 1 part solution to 20 parts water before use.

A container of the solution is connected to agricultural sprayer equipment, and sprayed through a hollow cone spray nozzle at a pressure of 250 psi. The spray droplet size is 100–150 microns. A field of ornamental evergreen saplings is sprayed with the solution, and is effective for preventing fungal infection of the trees, and for promoting vigorous growth.

What is claimed is:

1. A method of controlling fungal disease in agricultural and horticultural applications which comprises (1) water-diluting a concentrated aqueous fungicidal fertilizer formulation having a solution content comprising (a) about 0.1–25 weight percent of an ingredient selected from the group consisting of at least two alkali metal and ammonium bicarbonates; (b) about 0.05–50 weight percent of an ingredient selected from the group consisting of alkali metal and ammonium salts of $C_8$–$C_{22}$ fatty acids; (c) about 0.01–5 weight percent of a water-soluble pseudoplastic thickener ingredient; and (d) about 0.1–25 weight percent of an ingredient selected from phosphorus-containing compounds; based on the composition weight; wherein the composition ingredients have a formulated fertilizer ratio of nitrogen, phosphorus and potassium elements; and (2) applying the diluted fungicidal fertilizer formulation to cultivated plants.

2. A method in accordance with claim 1 wherein the applied aqueous formulation additionally contains between about 1–30 weight percent of an ingredient selected from the group consisting of sodium, potassium, lithium and ammonium carbonates, based on the weight of bicarbonate ingredient, and the aqueous formulation has a pH in the range of 7.5–12.

3. A method in accordance with claim 1 wherein the aqueous formulation additionally has a content of water-soluble sulfur-containing ingredient.

4. A method in accordance with claim 1 wherein the aqueous formulation additionally has a content of urea which provides nitrogen element in the formulated fertilizer ratio.

5. A method in accordance with claim 1 wherein the aqueous formulation additionally has a content of dipotassium orthophosphate which provides phosphorus and potassium elements in the formulated fertilizer ratio.

* * * * *